United States Patent [19]

Cragoe, Jr. et al.

[11] 4,428,959

[45] Jan. 31, 1984

[54] 4-ALKYLSUBSTITUTED-3-HYDROXY-3-PYRROLINE-2,5-DIONE INHIBITORS OF GLYCOLIC ACID OXIDASE

[75] Inventors: Edward J. Cragoe, Jr., Lansdale; Clarence S. Rooney, Worcester, both of Pa.

[73] Assignee: Merck & Co., Inc., Rahway, N.J.

[21] Appl. No.: 137,345

[22] Filed: Apr. 4, 1980

[51] Int. Cl.$^3$ .................. A61K 31/40; C07D 207/456
[52] U.S. Cl. ..................................... 424/274; 548/544
[58] Field of Search ............. 260/326.5 FM; 424/274; 548/544

[56] References Cited

U.S. PATENT DOCUMENTS

| | | | |
|---|---|---|---|
| 3,129,225 | 4/1964 | Shapiro et al. | 260/326.5 FM |
| 3,338,911 | 8/1967 | Schäfer | 260/326.5 FM |
| 3,340,263 | 9/1967 | Staehelin et al. | 260/326.5 FM |
| 3,948,941 | 4/1976 | Patton | 260/326.5 FM |
| 4,194,982 | 3/1980 | Chou | 260/326.5 FM |

OTHER PUBLICATIONS

Liao, et al., "Arch. Biochem. Biophys.", vol. 154, 1973, pp. 68–75.
Harlay, "J. Pharm. Chim.", vol. 24, 1936, pp. 537–548.
Skinner, et al., "J. Am. Chem. Soc.", vol. 73, 1951, pp. 2230.
Skinner, "J. Am. Chem. Soc.", vol. 70, 1948, pp. 4011.

*Primary Examiner*—Donald G. Daus
*Assistant Examiner*—James H. Turnipseed
*Attorney, Agent, or Firm*—Raymond M. Speer; Theresa Y. Cheng

[57] ABSTRACT

Novel 4-alkylsubstituted-3-hydroxy-3-pyrroline-2,5-diones are disclosed which inhibit glycolic acid oxidase and thus are useful in the treatment and prevention of calcium oxalate kidney stone formation. A novel process for their preparation is also disclosed.

8 Claims, No Drawings

4-ALKYLSUBSTITUTED-3-HYDROXY-3-PYRROLINE-2,5-DIONE INHIBITORS OF GLYCOLIC ACID OXIDASE

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common forms of treatment for renal lithiasis due to calcium oxalate consist of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of metabolically derived oxalate in the urine of a typical patient is glyoxylic acid. In turn its most important precursor is glycolic acid. The enzyme glycolate oxidase is able to carry oout the oxidation of glycolic acid, through glyoxylic acid, to oxalic acid. Inhibition of this enzyme will, therefore, reduce the concentration of oxalic acid in the kidney and bladder, decreasing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

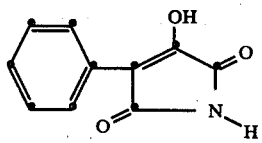

has been described by Harlay, *J. Pharm. Chim.*, 24, 537–48 (1936). 3-Hydroxy-4-aryl-3-pyrroline-2,5-diones are described in U.S. Pat. No. 3,340,263 as intermediates in the preparation of antiphlogistic substances. A number of 3-hydroxy-4-substitutedphenyl-3-pyrroline-2,5-diones are reported by G. S. Skinner et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., *J. Am. Chem. Soc.*, 70, 4011 (1948).

SUMMARY OF THE INVENTION

It has now been found that novel compounds of the formula:

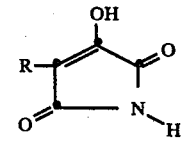

wherein
R is straight or branched chain alkyl groups having from 6 to 16 carbon atoms, or more particularly R can be $CH_3(CH_2)_n$ when n=5–15 or

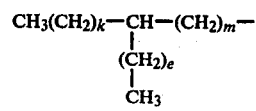

wherein $k+e+m=3$ to 13
or a pharmaceutically acceptable salt thereof are potent inhibitors of glycolate oxidase. They are, therefore, useful in the treatment and prevention of calcium oxalate kidney and bladder stone formation.

DETAILED DESCRIPTION

About 70% of all renal calculi contain oxalate as the main anion component of the matrix. In the majority of patients urinary oxlate is predominantly of metabolic origin. With typical stone formers urinary oxlate levels lie on the high end of the normal range. The major pathway for biosynthesis of oxalate can be represented as follows:

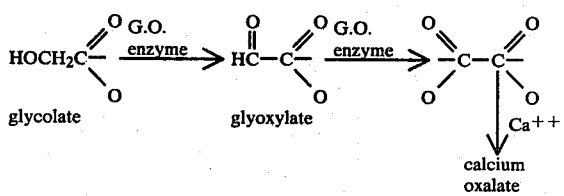

Glyoxylate is the most important immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may also be useful in the treatment of the genetically inherited diseases termed Hyperoxaluria types I and II. in which abnormally high levels of oxalate are observed.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificty against SRS-A. SRS-A is considered a major mediator in human allergic asthma. Thus the compounds of formula (I) are useful in the treatment of allergy, especially allergic asthma.

Compounds of Formula (I) can be prepared according to the following novel route:

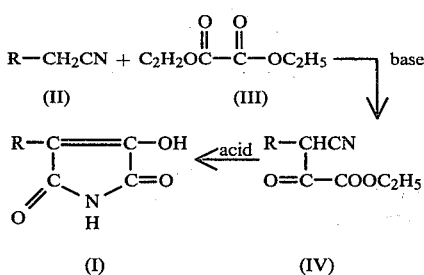

wherein R is as previously defined.

Thus an alkyl cyanide I is reacted with a diethyl oxalate III to form an intermediate 3-cyano-2-keto alkanoic acid ethyl ester IV which is then converted to the desired product I by an acid catalyzed hydrolysis and ring closure reaction. (Compound IV can also exist in the enolic form, while compound I can exist as the tantomeric pyrrolidine-2,3,5-trione. The preference of I is for the 4-substituted-3-hydroxy-3-pyrroline-2,5-dione form).

The reaction for the preparation of the intermediate compound IV is carried out in the presence of a base such as for example potassium t-butoxide in an organic solvent, particularly an alcoholic or aprotic solvent such as, for example, dimethylformamide at room temperature to 60° C. for a sufficient time (4 to 24 hours) to form the desired intermediate II. Generally an equal molar ratio of the starting materials II and III and a slight molar excess of base are used. The intermediate IV is isolated from the reaction mixture by methods known in the art such as by acidification followed by extraction of the intermediate into an organic solvent and concentration of the solvent.

To prepare the desired product I, the 3-cyano-2-ketoalkanoic acid ethyl ester IV is subjected to an acid catalyzed hydrolysis and ring closure reaction by initially reacting said intermediate IV with a strong acid such as methanesulfonic acid followed by addition of an alcohol water mixture such as an ethanol water mixture. This reaction in strong acid is run for anywhere from 12 to 24 hours and at a temperature from room temperature to 60° C. after which time the alcohol-water is added. The desired product I is isolated from the reaction mixture by known methods such as by evaporation of the alcohol followed by extracting the desired product I into chloform and concentrating the chloroform to dryness, followed by recrystallization.

EXAMPLE 1

3-Hydroxy-4-(n-decyl)-3-pyrroline-2,5-dione 0.5 Moles of n-undecyl cyanide and 0.5 moles of diethyl oxalate are mixed in 1,000 ml of dimethylformamide. To this solution is added with ice cooling 0.52 moles of potassium t-butoxide. The mixture is allowed to stir overnight at room temperature. Following evaporation (rotary evaporator under vacuum) of most of the dimethylformamide the residue is mixed with 3 liters of diethyl ether followed by the addition of 1 liter water. The mixture is acidified with concentrated hydrochloric acid to a pH of 3 and then the ether phase is separated. After washing the ether with water and drying the ether over magnesium sulfate evaporation of the ether affords 3-cyano-2-oxotridecanoic acid ethyl ester. Recrystallization from petroleum ether at 30°–60° C. provides pure material.

1 G. of the 3-cyano-2-oxotridecanoic acid ethyl ester is dissolved in 5 ml of methanesulfonic acid and the mixture allowed to stand overnight at room temperature. The reaction mixture is worked up by first pouring into ethanol-water (20 ml ethanol—5 ml water). After standing for several hours, the ethanol is removed by evaporation. The aqueous acidic residue is diluted further with water and then extracted with chloroform. The chloroform solution is then washed well with water, dried and evaporated to give the desired 3-hydroxy-4-(n-decyl)-3-pyrroline-2,5-dione. Recrystallization from hexane or cyclohexane provides pure 3-hydroxy-4-(n-decyl)-3-pyrroline-2,5-dione, mp 109°–111° C.

Following the above procedure and using corresponding amounts of reactants except using n-octylcyanide in place of n-undecyl cyanide there is formed 3-cyano-2-oxodecanoic acid ethyl ester as an intermediate and 3-hydroxy-4-n-heptyl-3-pyrroline-2,5-dione as a final product.

EXAMPLE 2

Following the above procedure and using corresponding amounts of reactants except using n-heptadecylcyanide in place of n-undecylcyanide there is formed 3-cyano-2-oxononadecanoic acid ethyl ester as an intermediate and 3-hydroxy-4-n-hexadecyl-3-pyrroline-2,5-dione as a final product.

EXAMPLE 3

3-Hydroxy-4-(n-dodecyl)-3-pyrroline-2,5-dione 0.5 Moles of n-tridecyl cyanide and 0.5 moles of diethyl oxalate are mixed in 1,000 ml of dimethylformamide. To this solution is added with ice cooling 0.52 moles of potassium t-butoxide. The mixture is allowed to stir overnight at room temperature. Following evaporation (rotary evaporator under vacuum) of most of the dimethylformamide the residue is mixed with 3 liters of diethyl ether followed by the addition of 1 liter water. The mixture is acidified with concentrated hydrochloric acid to a pH of 3 and then the ether phase is separated. After washing the ether with water and drying the ether over magnesium sulfate evaporation of the ether affords 3-cyano-2-oxopentadecanoic acid ethyl ester. Recrystallization from petroleum ether at 30°–60° C. provides pure material.

1 G. of the 3-cyano-2-oxopentadecanoic acid ethyl ester is dissolved in 5 ml of methanesulfonic acid and the mixture allowed to stand overnight at room temperature. The reaction mixture is worked up by first pouring into ethanol-water (20 ml ethanol—5 ml water). After standing for several hours, the ethanol is removed by evaporation. The aqueous acidic residue is diluted further with water and then extracted with chloroform. The chloroform solution is then washed well with water, dried and evaporated to give the desired 3-hydroxy-4-(n-dodecyl)-3-pyrroline-2,5-dione. Recrystallization from hexane or cyclohexane provides pure 3-hydroxy-4-(n-dodecyl)-3-pyrroline-2,5-dione, mp 108°–109° C.

Following the above procedure and using corresponding amounts of reactants except using 4-ethylhexylcyanide in place of n-tridecyl cyanide there is formed 3-cyano-2-oxo-6-ethyloctanoic acid ethyl ester as an intermediate and 3-hydroxy-4-(3-ethyl-1-pentyl)-3-pyrroline-2,5-dione as a final product.

EXAMPLE 4

Following the above procedure and using corresponding amounts of reactants except using 5-propyloctyl-cyanide in place of n-tridecylcyanide there is formed 3-cyano-2-oxo-7-propyldecanoic acid ethyl ester as an intermediate and 3-hydroxy-4-[4-(n-propyl)-1-heptyl]-3-pyrroline-2,5-dione as a final product.

Included within the scope of the invention are the pharmaceutically acceptable salts of formula (I) compounds. The compounds of formula (I) are organic acids with pKa's in the range 3-5. These salts are readily formed with the usual inorganic cations such as sodium, potassium and ammonium. Salts with organic amines such as trimethylamine, triethylamine, n-butylamine and the like are also stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose in humans will be in the 30 to 2000 mg range with the preferred dosage range being 50 to 1000 mg.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose or lactose; a flavoring agent such as peppermint, oil of wintergreen or cherry. When the dosage unit form is a capsule, it may contain in addition to materials of the above type a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

What is claimed is:

1. A compound of the formula:

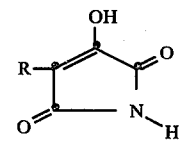

wherein R is a straight or branched chain alkyl group having from 6 to 16 carbon atoms or pharmaceutically acceptable salts thereof.

2. A compound of the formula:

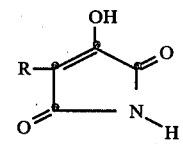

wherein R is $CH_3(CH_2)_n$- or $CH_3(CH_2)_k$-CH-$(CH_2)_m$-

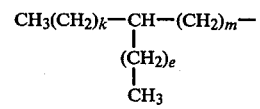

and n is 5-15 and k+e+m are 3-13 or pharmaceutically acceptable salts thereof.

3. A compound of claim 2 designated 3-hydroxy-4-(n-decyl)-3-pyrroline-2,5-dione.

4. A compound of claim 2 designated 3-hydroxy-4-(n-dodecyl)-3-pyrroline-2,5-dione.

5. A pharmaceutical composition comprising an effective amount of a compound of claim 1 or the pharmaceutically acceptable salts thereof and a pharmaceutically acceptable carrier thereof.

6. A pharmaceutical composition comprising an effective amount of a compound of claim 2 or the pharmaceutically acceptable salts thereof and a pharmaceutically effective carrier therefor.

7. A method of treating persons afflicted with calcium oxalate kidney or bladder stones or preventing the formation of calcium oxalate kidney or bladder stones which comprises administering to such a patient an effective amount of a compound of claim 1.

8. A method of treating persons afflicted with calcium oxalate kidney or bladder stones, or preventing the formation of kidney or bladder stones, which comprises administering to such a patient an effective amount of a compound of claim 2.

* * * * *